United States Patent [19]

Murr

[11] 4,146,311
[45] Mar. 27, 1979

[54] AUTOMATIC VISUAL FIELD MAPPING APPARATUS

[75] Inventor: William C. Murr, Piedmont, Calif.
[73] Assignee: Synemed, Inc., Berkeley, Calif.
[21] Appl. No.: 794,702
[22] Filed: May 9, 1977
[51] Int. Cl.² ............................................. A61B 3/06
[52] U.S. Cl. ................................................... 351/24
[58] Field of Search ....................... 351/24, 23, 30, 35, 351/36, 39

[56] References Cited

U.S. PATENT DOCUMENTS

| 3,172,404 | 3/1965 | Copenhaver | 351/24 X |
| 3,300,269 | 1/1967 | Schultz | 351/24 |
| 3,883,235 | 5/1975 | Lynn et al. | 351/39 |

*Primary Examiner*—Paul A. Sacher
*Attorney, Agent, or Firm*—Harris Zimmerman

[57] ABSTRACT

A device for automatically mapping the visual field of a subject includes a concave, generally hemispherical viewing screen, with a plurality of light-conducting fibers extending thereto from the convex side of the screen. The other ends of the light conducting fibers are joined to a light distribution board which includes a pivot supporting a scanning arm. The scanning arm includes a light conducting tube which is adapted to direct a beam of light into individual ends of the light conducting fibers, and the distribution board includes a printed circuit which is used to determine which light conducting fiber is being illuminated. The scanning arm itself is illuminated by a light module which includes an incandescent bulb powered by a regulated source, a continuously variable neutral density wedge, a color filter wheel, and a noiseless shutter. The light module also includes a light thief which samples the illumination provided to the scanning arm to determine the intensity thereof. Photoelectric means are provided to measure the actual background illumination of the viewing screen, and eye monitor means are provided to determine that the eye of the subject is open and is fixated on the center of the viewing screen.

16 Claims, 12 Drawing Figures

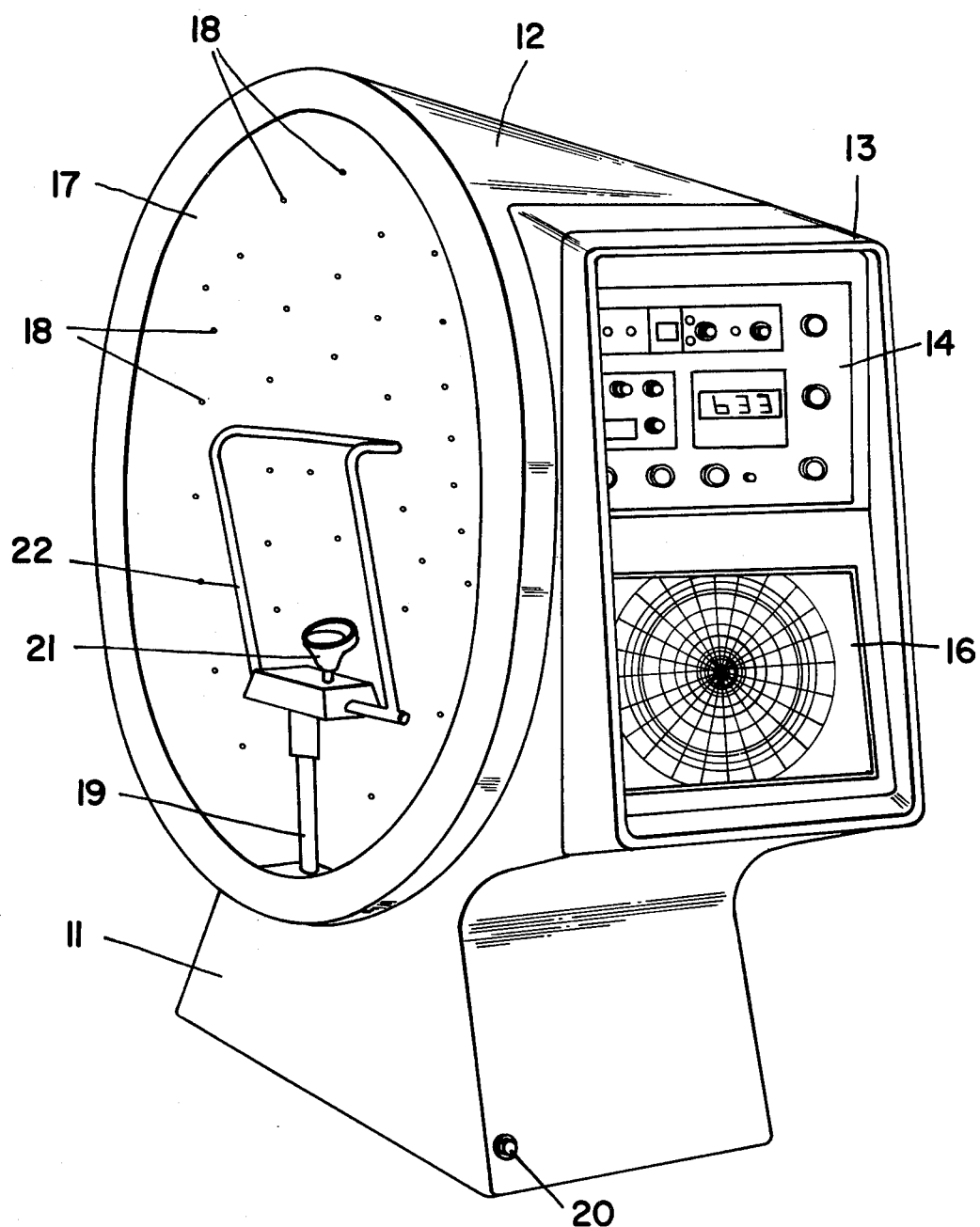
FIG_1

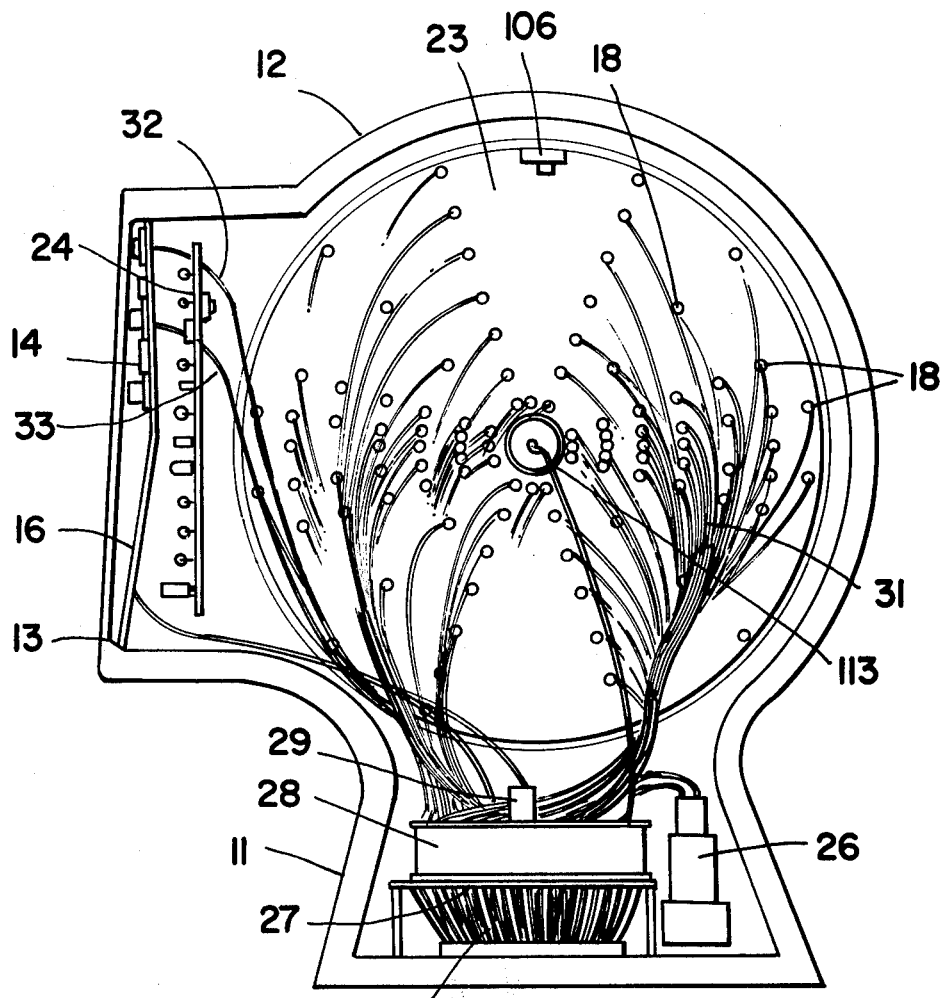
FIG_2
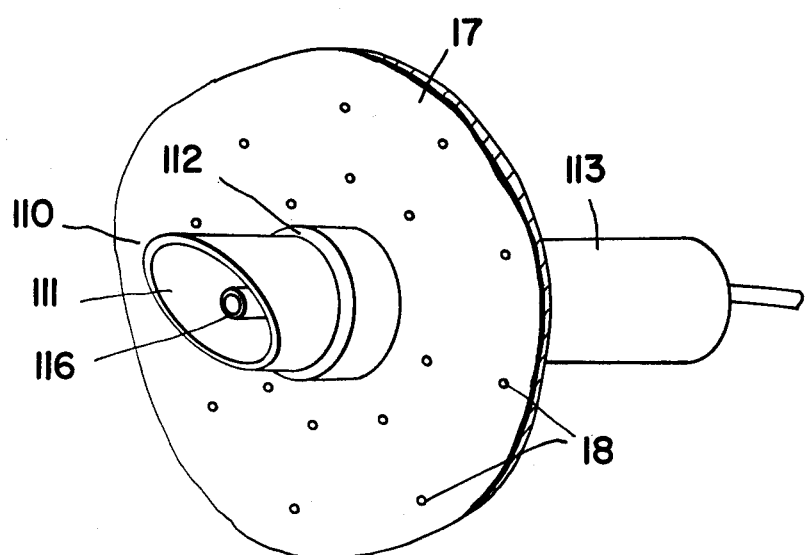
FIG_10

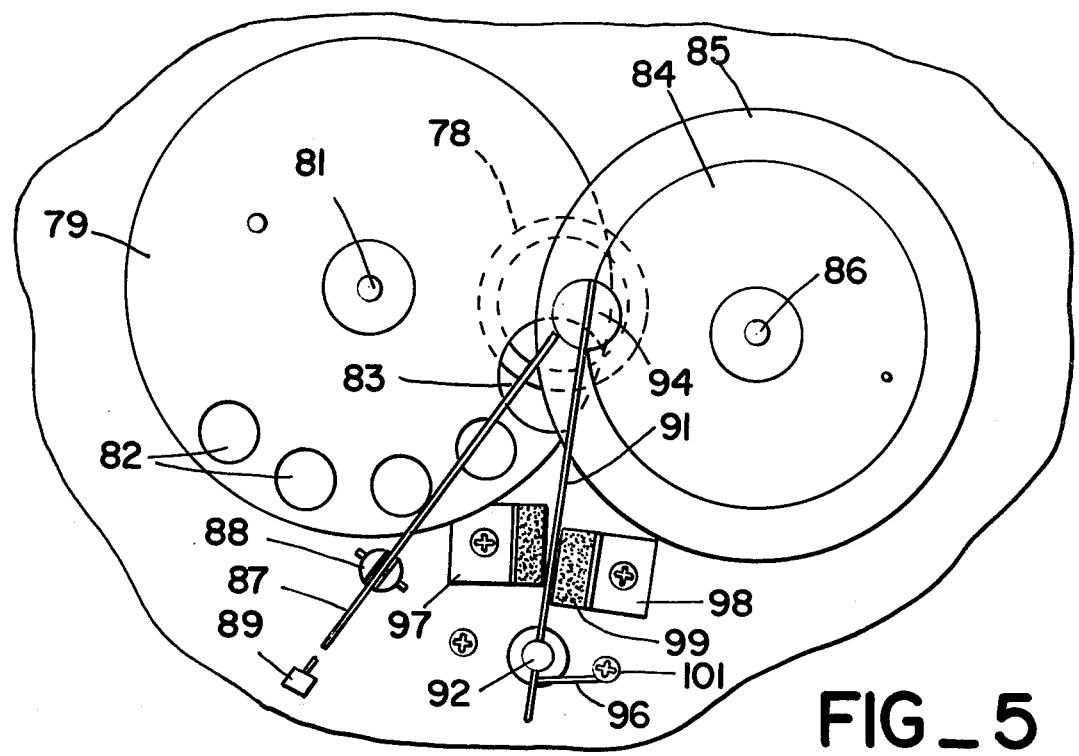
FIG_5
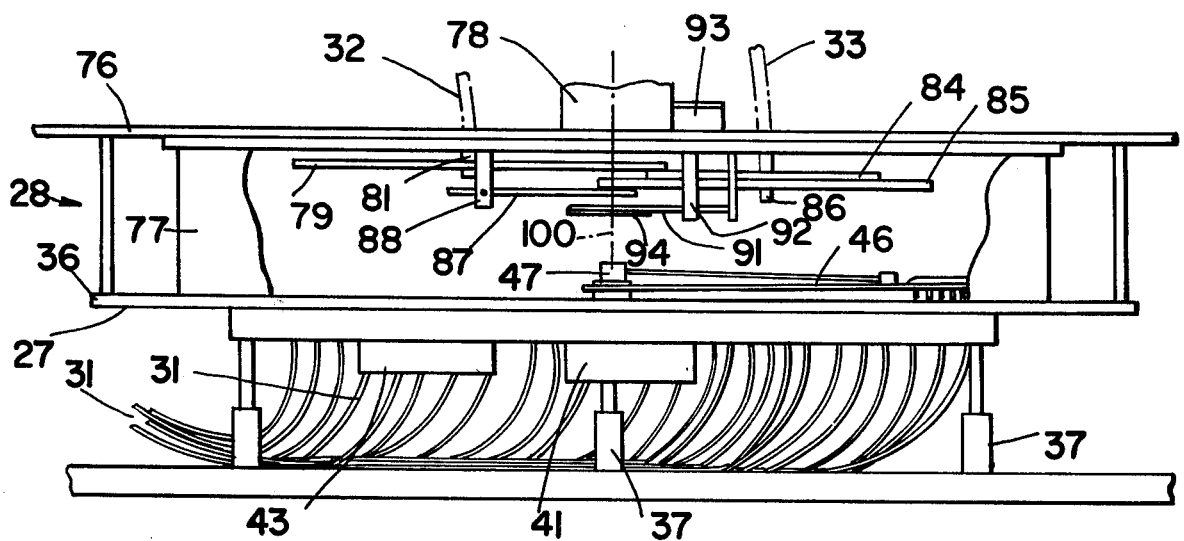
FIG_4
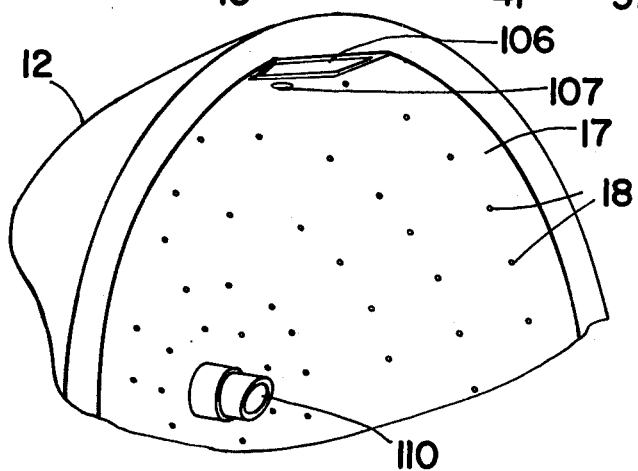
FIG_3

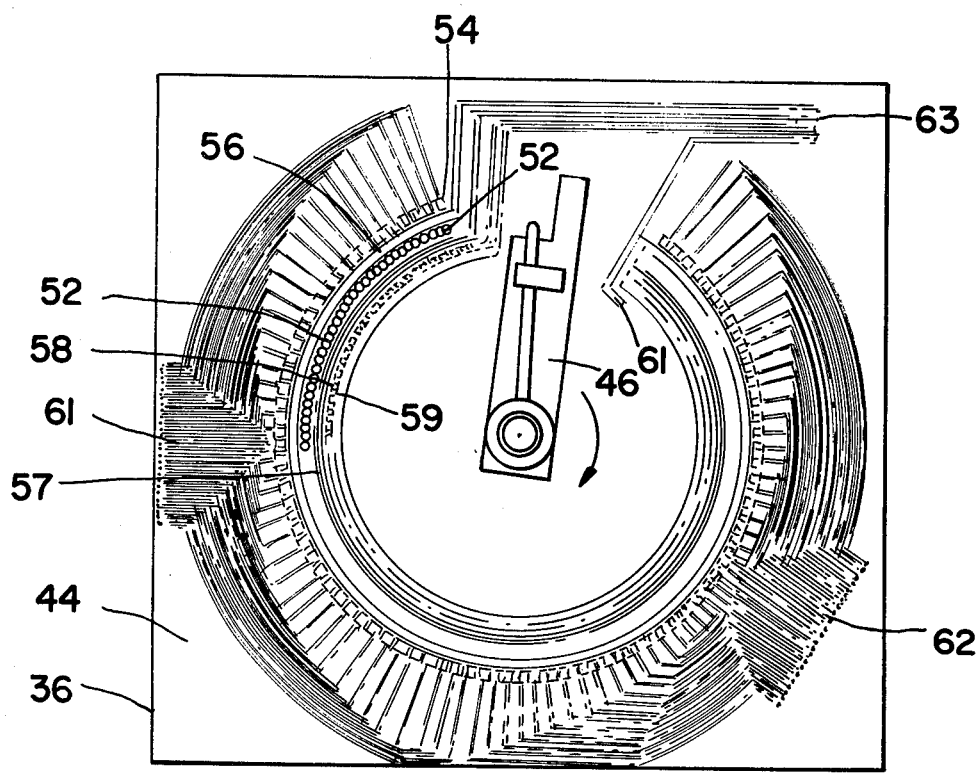
FIG_6
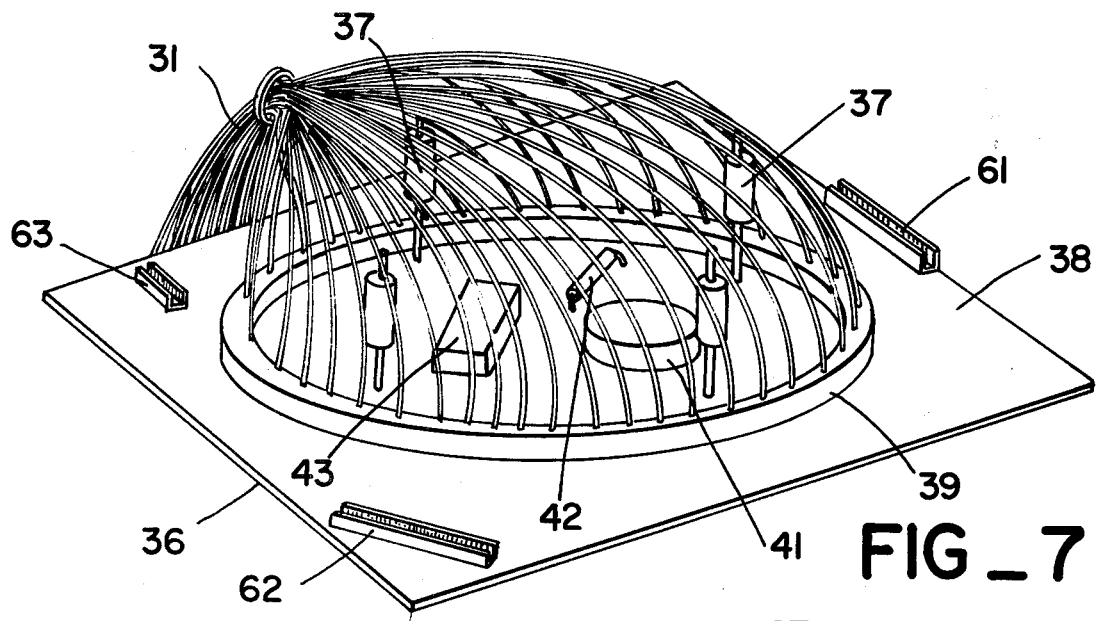
FIG_7
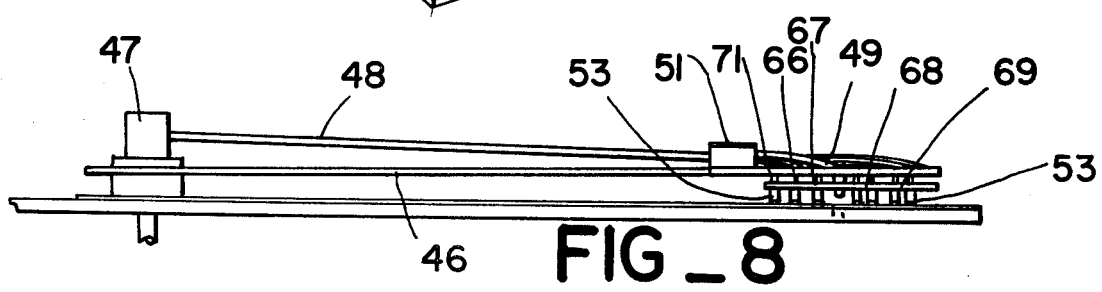
FIG_8

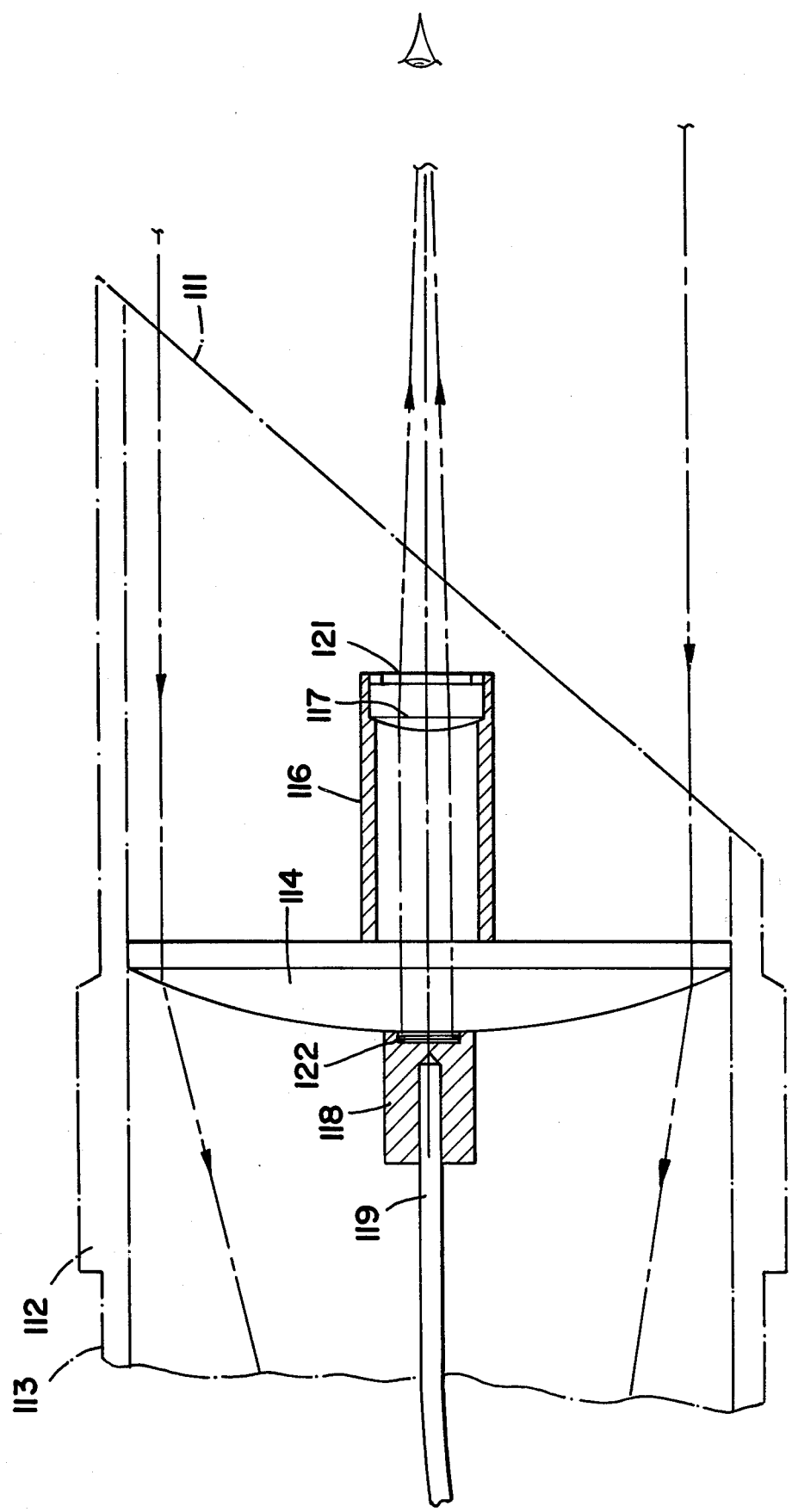
FIG_9

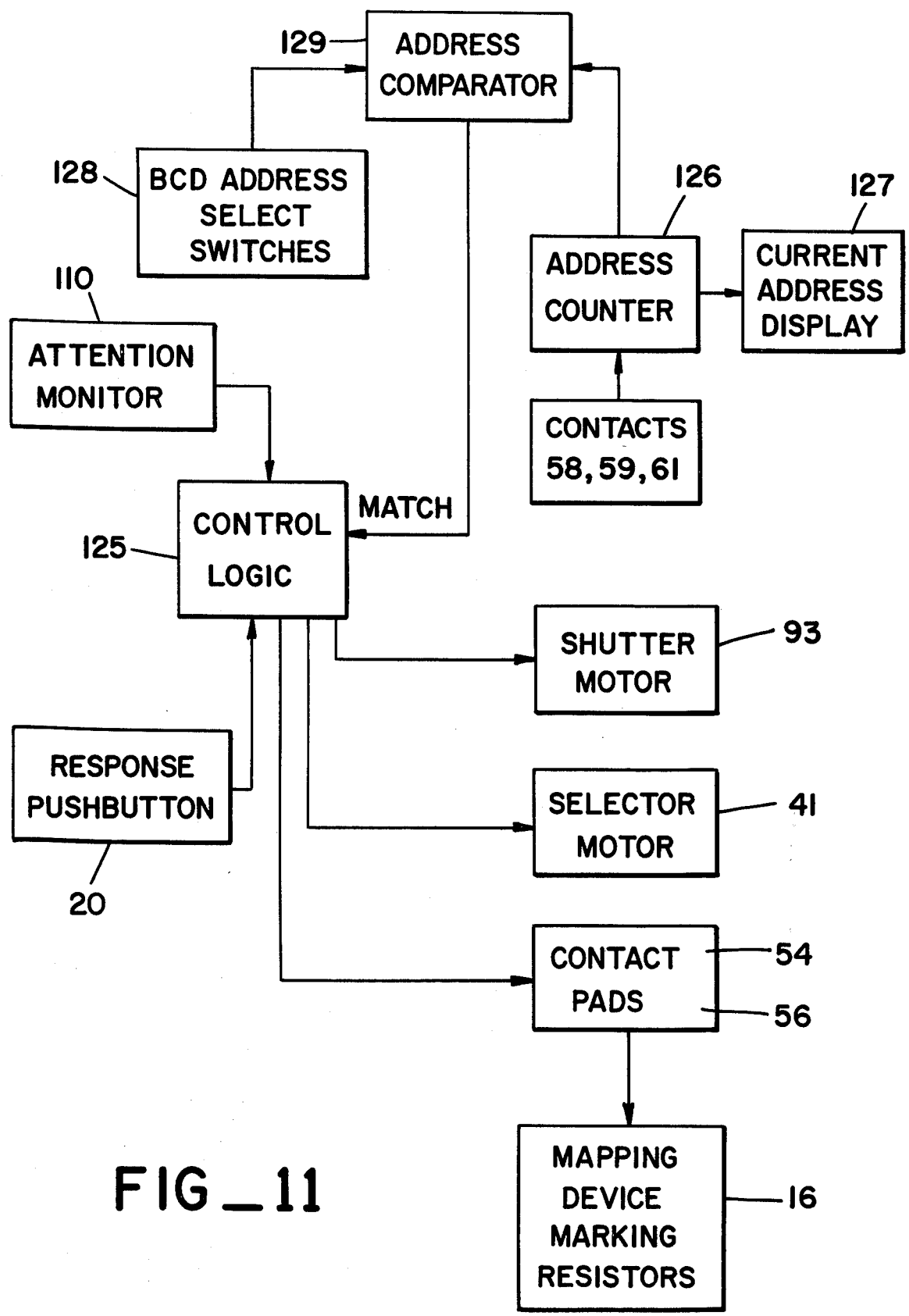
FIG_11

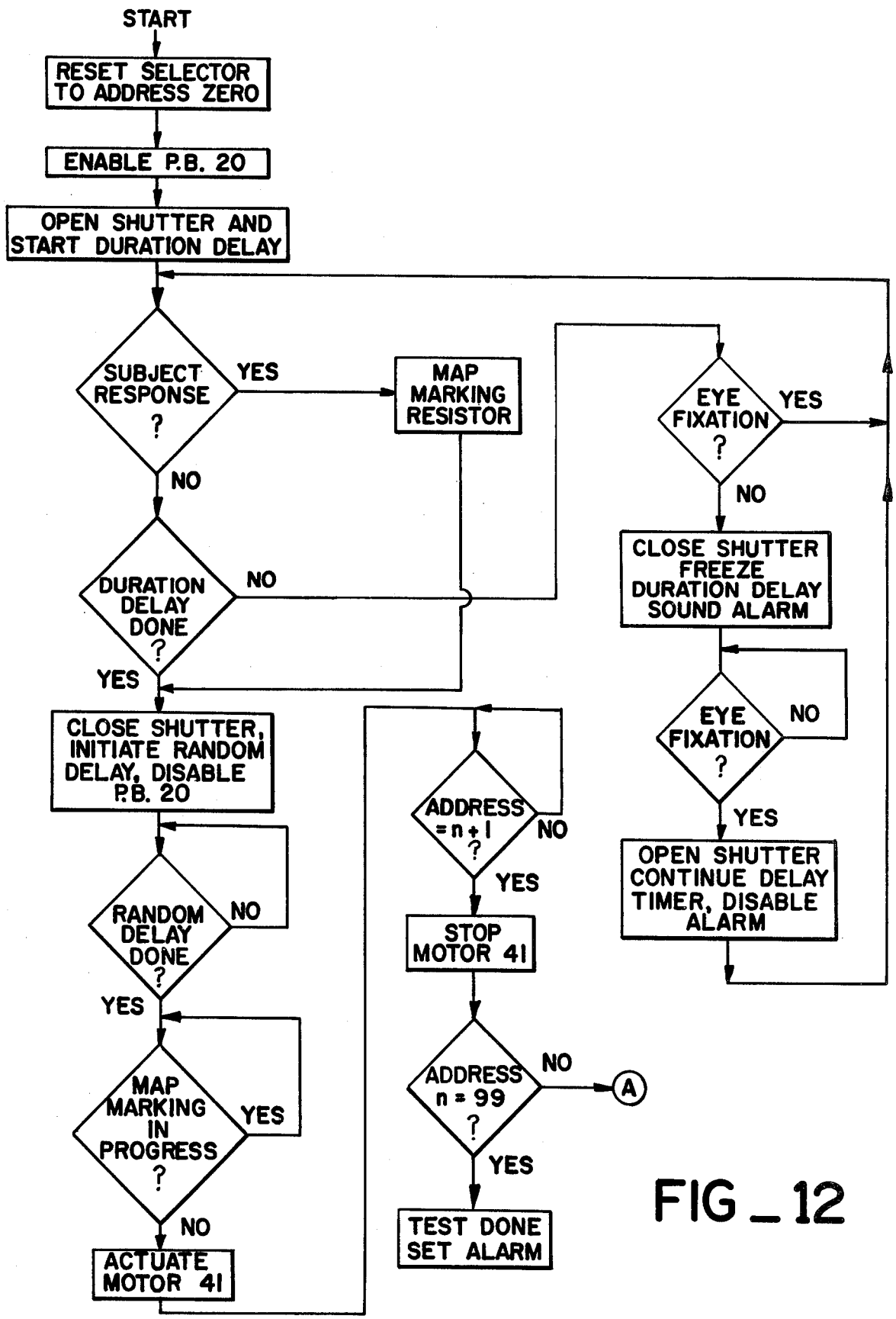
FIG_12

AUTOMATIC VISUAL FIELD MAPPING APPARATUS

BACKGROUND OF THE INVENTION

The visual field is defined in general terms as the solid angle, with the apex at the aperture of the eye, through which vision is obtained. The visual field is approximately conical in a healthy individual, although slight variations in the shape of the visual field are common. It has been found that severe variations or disruptions in the shape of the visual field are often indicative of disease. Thus, the mapping of the visual field of an individual is an important tool in diagnosing such diseases as lesions and tumors of the brain, and defects in the retina and optic nerve.

The mapping of the visual field of the subject has always been approximate, due to the inaccuracies inherent in the methods of mapping. The most basic mapping technique is to provide a wall having a target screen, the target screen including a central fixation target and solid angle indicators. A moving spot of light is scanned across the target screen by the operator, who asks the individual when the spot disappears and when it can be seen. The operator must also ascertain that the subject is maintaining fixation on the central fixation target.

The opportunities for error in this method of visual field mapping are manifest, due primarily to the subjectiveness of the method of testing. It is difficult to ascertain that the subject is maintaining fixation on the central target, and it is also difficult to ascertain that the subject is truthfully responding to the test. Furthermore, the actual luminance of the moving spot, and the background illumination of the target screen, are rarely if ever measured. Thus the moving spot contrast level, which is quite important in determining the sensitivity as well as the area of the visual field, is unknown.

In more modern visual field mapping devices, a hemispheric screen is provided, with the head of the subject supported so that the eye is at the center of the hemisphere. A plurality of light emitting diodes may be selectively spaced about the hemisphere, and individually actuated to test the visual response of the eye. However, it is extremely difficult to vary the color of light emitting diodes, so that the visual field as a function of color cannot be mapped.

In other forms of visual field mapping devices known in the prior art, light conducting fibers extend from the back side of a hemispheric screen. The other ends of the light conducting fibers are joined to a board in a circular array, with the pivot of a light crank at the center thereof. The light crank is incremented to illuminate individual light conducting fibers, the crank being operated by a one-rotation clutch operated mechanism. Illumination is provided by an incandescent bulb which is driven by a variable transformer to vary the luminance selectively; filters and a shutter are also provided in the light path.

Although this prior art device appears to be quite sophisticated, it suffers from the same drawback as the crudest visual field mapping method. That is, there is no means for ascertaining the luminance level of the spots of light, and no control over the background illumination of the screen. The luminance level may be affected by the age of the incandescent bulb, dust in the optical system, and fluctuations of the line current supply. These variations significantly effect the outcome of the visual field mapping procedure, and are completely ignored.

Furthermore, there is no provision for ascertaining the exact position of the light crank with respect to the light fibers which it illuminates. As the light crank increments through one hundred positions to illuminate as many light fibers, cumulative errors in position may cause it to illuminate an incorrect light fiber, or to illuminate two light fibers at one time, or the like. These errors also are undetected.

Due to the inaccuracies of all of the prior art visual field mapping devices, it is impossible to replicate mapping tests with any degree of certainty. Mapping tests made on different devices or at different times may bear no relationship with other visual field maps for the same individual. Thus, most of the field mapping data which is accumulated is virtually worthless. Only the most gross visual field distortions can be considered significant. Subtle variations in visual field, or progressive variations indicative of progressive disease, cannot be detected.

SUMMARY OF THE PRESENT INVENTION

The present invention generally comprises a visual field mapping device which is designed to record automatically and accurately the visual field of a subject. The invention is specifically intended to overcome the error causing drawbacks of the prior art, so that visual field mapping tests may be replicated with great accuracy, and so that many more of the visual field mapping data may be regarded as significant.

The invention includes a viewing screen comprising the inner surface of a hemisphere, with a plurality of light conducting fibers extending through the back side of the hemisphere to the viewing screen. The other ends of the light conducting fibers are secured in circular array to a light distribution board having a scanning arm secured to a pivot shaft at the center of the circular array. The distribution board includes a circuit printed thereon having contact points adjacent to each of the ends of the light conducting fibers, and the scanning arm includes brushes for bridging the contact points and thus providing information position to logic circuitry. The exact position of the scanning arm can thus be determined at any given time. The scanning arm also includes a light conducting pipe which illuminates each end of each light conducting fiber individually. The scanning arm is driven by an electric motor, and a feedback loop from the logic circuitry actuates a brake to stop the scanning arm pivot shaft with the light conducting pipe in exact registration with any light conducting fiber at any desired location on the circle.

Illumination is provided to the scanning arm by means of a light module which is directly superjacent to the light distribution board. The light module includes an incandescent bulb which is driven by a regulated power source to provide constant illumination. The light module includes a color filter wheel, and a continuously variable neutral density wheel, both of which are selectively rotatable by direct mechanical linkage to a control panel.

The light module also includes a noiseless shutter mechanism which selectively interferes with the light path to block any illumination to the light scanning arm. The light module further includes a light thief; that is, a light conducting fiber extending into a portion of the light beam from the incandescent bulb. The light thief is disposed downstream from the color filter and neutral density filter, and is connected to a photocell which accurately measures the illumination which is being provided to the scanning arm and thus to the individual light conducting fibers. The photocell signal is conducted to a meter on the control panel which continuously apprises the operator of the exact luminance of the stimulus spots.

A second photocell pickup within the hemispheric screen measures the background illumination of the screen, and drives the same meter on the control panel. The operator thus can monitor both the luminance of the stimulus and the background illumination so that the contrast level therebetween may be adjusted to any desired level. Furthermore, variations in the stimulus luminance due to dust in the optical path, aging of the incandescent bulb, or the like, may be compensated by use of the continuously variable density wedge. Furthermore, unlike prior art devices, the incandescent bulb may be replaced with any similar incandescent bulb, since the luminance level is measurable and adjustable.

The invention includes a mapping device used in conjunction with a thermosensitive map having a circular representation of the stimulus points on the hemispheric screen. A plurality of heating resistors, one for each stimulus point, are disposed behind the thermosensitive map. The test subject is provided with a button which is depressed whenever a stimulus point is observed. The button closes a circuit which extends through the light distribution board to heat the resistor corresponding to the observed illuminated point. The heated resistor causes a mark to be made on the map to indicate that the stimulus point has been observed.

The invention includes automatic testing circuitry which periodically causes the scanning arm to advance to the next testing point, and opens the shutter to illuminate the succeeding stimulus point. The automatic testing circuitry includes a random time delay factor which thwarts any attempt on the part of the test subject to guess when a stimulus point is illuminated by means of the rhythm of the automatic test sequence. The random time delay factor, in combination with the noiseless shutter and noiseless scanning arm mechanism, assure that only visual stimulus is provided to the test subject.

Disposed in the topographical center of the viewing screen is an eye attention monitor. The eye attention monitor includes a telescope disposed coaxially about an eye fixation target. The fixation target is illuminated through a light conducting fiber by a separate light source having a unique color, such as red. The fixation target may be interrupted periodically to renew the stimulus of the fixation and thus maintain eye fixation on the center of the screen.

The telescope of the eye attention module is directed at the iris of the eye of the subject. The image of the iris falls on a photoelectric pickup, and the output of the photoelectric pickup is connected to the automatic testing circuitry. Should the test subject blink or look away from the eye fixation target, the image of the iris which falls on the photoelectric pickup will vary, and the automatic testing circuitry will interrupt the test sequence. The test subject may rest the eye being tested merely by closing the eyelid for as long as is desired. Thus, eye fatigue is removed as a significant parameter in testing data, as are errors due to wandering fixation of the eye.

BRIEF DESCRIPTION OF THE DRAWING

FIG. 1 is a perspective view of the visual field mapping device of the present invention.

FIG. 2 is a cut-away back view of the visual field mapping device of the present invention.

FIG. 3 is a front perspective view of a portion of the viewing screen of the present invention.

FIG. 4 is a rear elevation of the light module and light distribution module of the present invention.

FIG. 5 is an inverted bottom view of the light module shown in FIG. 4.

FIG. 6 is a top view of the light distribution board of the present invention.

FIG. 7 is an inverted bottom view of the light distribution board of the present invention.

FIG. 8 is a side view of the scanning arm of the light distribution module of the present invention.

FIG. 9 is a cross-sectional elevation of the eye attention module of the present invention.

FIG. 10 is a perspective view of the eye attention module of the present invention.

FIG. 11 is a block diagram of the inter-relationship of the control apparatus of the present invention.

FIG. 12 is a flow chart depicting the algorithm of the control apparatus shown in FIG. 11.

DESCRIPTION OF THE PREFERRED EMBODIMENT

As shown in FIG. 1, the visual field mapping device of the present invention generally includes a housing 12 supported on a pedestal base 11 which is adapted to rest on a table stand or the like. The housing 12 has a generally ovoid configuration, with a rectangular extension 13 protruding from one side thereof. The face of the extension 13 includes a control panel 14 and a map fabricating section 16.

The front face of the visual field mapping device includes a concave viewing screen 17 which is provided with a hemispheric configuration. Disposed in predetermined locations about the viewing screen 17 are a plurality of visual stimulus points 18 which are selectively illuminable, as will be described in the following. A support member 19 extends upwardly from the lowermost portion of the viewing screen 17, and supports a headrest which includes a chin rest 21 and a head brace 22. The head rest supports the head of the subject being tested by the visual field mapping device, and it is adjustable to place either of the eyes of the subject exactly in the center of the hemispheric screen 17. A pair of normally opened push-button switches 20 are disposed at either side of the pedestal base 11, and are depressed by the test subject during the course of the automatic testing procedure as will be explained.

As shown in the rear view of FIG. 2 with the back panel removed, the invention includes a plurality of light conducting fibers 31, each having one end extending through the back surface 23 of the viewing screen and connected to one of the visual stimulus points 18. The other end of the light conducting fibers are connected to the underside of a light distribution module 27 which is supported within the hollow pedestal base 11. Supported superjacently upon the light distribution module 27 is a lighting module 28, which includes a light source 29 extending upwardly therefrom. Adjacent to the modules 27 and 28 and within the base 11 is a regulated power supply 26.

Disposed within the rectangular extension 13 are a plurality of circuit boards 24 comprising the electronic circuitry which operates the visual field mapping device. A pair of flexible rotatable cable links 32 and 33 extend from the control panel 14 to the top of the lighting module 28.

As shown in FIGs. 4 and 7, the light distribution module 27 includes a panel 36 which is supported by four spacers 37. The spacers 37 are disposed within an annular ring 39 which is secured to the underside 38 of the panel 36. The light conducting fibers 31 extend underneath the panel 36 and are joined in equally spaced relationship to the annular ring 39. The fibers extend through the ring 39 and the panel 36, with the ends of the fibers disposed flush with the upper surface 44 of the panel. Also joined to the underside 38 of the panel is a relay 43, a resistor 42, and an electric motor 41. The shaft of the motor 41 extends through the board to the upper surface thereof, the relay 43 is connected to the motor for selective actuation thereof, and the resistor 42 is provided for its damping effect on the operation of the motor.

With reference to FIGS. 4, 6, and 8, a scanning arm 46 is disposed directly superjacent to the upper surface 44 of the panel 36, and is secured at one end to the shaft of the motor 41 for rotation thereby. A supporting cylinder 47 is joined to the upper surface of the arm 46, and is disposed coaxially with the shaft of the motor 41. A light conducting tube 48 is also secured to the arm 46, one end of the tube being connected to the cylinder 47 in light conducting fashion. The other end portion 49 of the tube 48 is provided with a 90° bend, so that the end of the tube is disposed in closely spaced relationship with the surface 44 of the panel 36. The end of the tube 48 is also disposed in registration with the circle 52, shown in FIG. 6, on which the optically receiving ends of the light conducting fibers 31 are disposed.

Disposed concentrically on the surface 44 of the panel 36 are a plurality of printed circuits. The arm 46 is provided with a plurality of brushes 53 which are disposed at the end of the arm, spaced radially inwardly and outwardly from the end portion 49 of the light conducting tube 48.

The outermost printed circuit comprises a ring of contact pads 54, each one aligned with a respective light fiber end on the circle 52. Extending from each contact pad 54 is a printed conductor which leads to one of the connector blocks 61 or 62. Spaced radially inwardly from the contact pads 54 and directly adjacent thereto is an annular contact strip 56. The outermost pair 69 of the brushes 53 are disposed to ride on the contact pads 54, impinging on one contact pad only at a time. The pair 68 of the brushes is disposed to ride on the contact strip 56, and the pairs 68 and 69 are interconnected on the arm itself. Thus the brushes 68 and 69 complete a circuit between one of the contact pads 54 and the strip 56.

Within the circle 52 there is disposed another annular contact strip 57. This contact strip is connected to ground, and is adapted to be contacted by a brush 67. Disposed concentrically within the contact strip 57 are a pair of contact strips 58 and 59. The outer strip 58 of the two is provided with a continuous annular ring from which a plurality of contact pads extend radially inwardly. Each of the contact pads extending from the strip 58 are aligned with one of the ends of the light conducting fibers on the circle 52. The strip 59 includes an annular conductor portion from which a plurality of contact pads extend radially outwardly. Each of the contact pads associated with conductor 59 are disposed midway between the contact pads of conductor 58. The brush 66 is disposed to contact the pads extending from conductors 58 and 59.

The panel 36 is also provided with a contact block 63, from which printed conductors extend to the annular contact rings 56, 57, 58, and 59. A printed conductor also extends to a contact pad 61 which is disposed at the beginning of the annular printed circuit array. The pad 61 comprises a zero reset conductor, and is adapted to be contacted by the brush 71 on the arm 46.

The map printing portion 16 of the present invention includes a plurality of heating resistors secured to a platen upon which a printed thermosensitive map is placed. The resistors are places on the platen in a circular format which is a two-dimensional representation of the placement of the stimulus light points on the three-dimensional hemispheric viewing screen. Each of the heating resistors is connected through contacts block 61 to one of the contact pads 54. The contact strip 56 is connected through contact block 63 to the push-button switch 20, and thence to a current supply. Thus, whenever the button 20 is pushed, upon viewing a stimulus lightpoint, the circuit is completed through the push button 20 and through the brushes 68 and 69 to heat the appropriate resistor and cause a mark to be burned on the map in the correct position.

The contact pads of the contact strips 58 and 59 are connected to set and reset inputs respectively, of an address counter within the logic circuitry. The brushes 66 and 67 bridge the grounding strip 57 and the strips 58 and 59, to ground the set and reset inputs of the address counter as the arm 46 rotates clockwise as viewed in FIG. 6. As the counter goes from set to reset and back to set, it increments one count, and it attains the set condition coincident with the optical alignment of the end 49 of the light conducting tube with one of the optically receiving ends of the light conducting fibers 31. At this time the logic circuitry stops the motor 41 so that the stimulus point corresponding to the particular light conducting fiber and the particular address held in the address counter can be tested. It may be appreciated that the address counter counts from zero to 100 in a serial manner.

The brush 71 is connected to the grounding brush 67, and is adapted to contact the zero reset pad 61. The zero reset pad is connected through contact block 63 to the zero reset input of the address counter. Thus, as the arm 46 begins its clockwise sweep, the brush 71 causes the address counter to reset to zero just before the brush 66 contacts the strips 58 and 59.

Alternatively, the printed contact strips may be replaced by grouped printed address contact strips, each radially adjacent to one of the light conducting fibers on the circle 52. Each group of contact strips represents a binary coded address associated with the adjacent light filter. The contacts are scanned by brushes 66 and 67, and the information is stored in an address register, providing absolute identification of the location of the scanning arm.

Illumination is provided to the scanning arm 46 by the lighting module 28, which is disposed directly superjacent of the panel 36. The lighting module includes a panel 76 which is parallel to and spaced apart from the panel 36, and a cylindrical housing 77 extending between the two panels. The housing 77 is joined to the panels 36 and 76 in a light-proof fashion, and it also includes acoustical insulation joined to the inner surface thereof.

With reference to FIGS. 4 and 5, a light source housing 78 extends upwardly from the upper surface of the panel 76 and is disposed generally coaxially with the housing 77. The light source housing 78 includes an incandescent bulb and a collimating lens which direct a beam of light through an axial aperture in the panel 76 and along an optical axis 100. It may be appreciated that the cylindrical block 47 of the scanning arm 46 is disposed on the optical axis 100 to receive the light beam from the light source.

A disc 79 is disposed within the housing 77, and is secured to a shaft 81 which extends through the panel 76. The disc 79 is disposed so that a portion thereof extends through the optical axis 100. The disc 79 includes a plurality of apertures 82 in which color filters or the like are disposed, and a larger apertures 83 having no filter at all. The apertures 82 and 83 are situated with their centers disposed on a circle which is concentric about the shaft 81. The circle intersects the optical axis 100, so that each aperture 82 or 83 may be brought into registration with the optical axis to allow the light beam from the housing 78 to pass therethrough.

The shaft 81 is connected to the flexible rotatable cable link 32, shown in broken line in FIG. 4 and in black line in FIG. 2. The other end of the cable link is connected to a knob on the control panel, which permits manual rotation of the cable link and thus of the disc 79. Thus, the operator of the testing device is able to select any of the colors provided by the color filters or white light provided by the aperture 83 to illuminate the stimulus test point.

A disc 84 is also disposed in the housing 77, secured axially to a shaft 86 which extends rotatably through the panel 76. The disc 84 includes an outer annular portion 85 which is disposed to intersect the optical axis 100 downstream from the disc 79. The annular portion 85 comprises a neutral density filter having a continuously variable transmissivity.

The upper end of the shaft 86 is coupled to the flexible rotatably cable link 33. The other end of the cable link 33 is connected to a knob on the control panel, as shown in FIG. 2. A test operator, rotating the associated knob, rotates the cable link 33 and the disc 86 to select the portion of the neutral density filter intersecting the optical axis 100 which has the desired transmissivity.

A device for measuring the intensity of the beam from the light source 78, or light thief is also secured within the housing 77. It includes a light tube 86 which is secured to the underside of the panel 76 by means of a gimbal mount 88. Joined to the distal end of the support tube 87 is a photoelectric cell 89, which is coupled to the beam of light emanating from the housing 78. The photoelectric cell 89 is disposed downstream of both the color filter disc 79 and the neutral density filter 85. Thus, it is illuminated with light having the same color and intensity as that which is received at the cylindrical block 47 on the scanning arm. The signal from the photoelectric cell 89 is conducted through wires leading from the panel 76 to the electronic circuitry 24. The output of the photoelectric cell 89 is amplified and displayed by a digital illuminance meter which is disposed on the control panel.

The lighting module is also provided with a shutter mechanism which comprises a tubular arm 91 joined at one end to a shaft 92. The shaft 92 extends through the panel 76 from an electric motor 93 mounted on the upper side thereof. Joined to the other end of the arm 91 is a disc 94 which is disposed perpendicularly to the optical axis 100, and is greater in diameter than the width of the light beam emanating from the housing 78. The shutter is disposed downstream of the photoelectric pickup, as shown in FIG. 4.

Disposed on either side of the arm 91 are a pair of stop brackets 97 and 98. Each stop bracket includes a downwardly depending portion to which a cushioning material 99 is secured. The cushioning material 99 is provided with a minimum spacing therebetween to limit the rotational movement of the arm 91 so that the disc 94 may undergo sufficient translation to block or unblock the light beam directed along axis 100. The cushioning material 99 stops the motion of the arm 91 without generating any audible noise, so that the test subject is given no auditory clue as to when a stimulus point on the viewing screen is illuminated.

Adjacent to the shaft 92 is a post 101. An elastic extension member 96 extends from the post 101 to the arm 91 adjacent the shaft 92, as shown in FIG. 5. The tension of the elastic member 96 biases the arm 91 to impinge on the cushion of the bracket 97, with the disc 94 blocking the light from the light source. The electric motor 93 rotates the shaft 92 and also acts as a constant torque source. That is, the motor 93 is actuated to rotate the shaft 92 clockwise as shown in FIG. 5, so that the disc 94 unblocks the light beam as the arm 91 impinges against and is stopped by the cushion of bracket 98. This motion is effected against the resilient tension of the elastic member 96. Actuation of the motor 93 is maintained so that the torque therefrom will sustain the arm 91 and disc 94 in the unblocked position, impinging on bracket 98. When the motor 93 is turned off, the elastic tension of member 96 will immediately cause the arm 91 to rotate back to the blocking position, impinging on the cushion of bracket 97. The shutter is then closed.

It should be noted that the shutter may be opened or closed for whatever time interval desired, merely by selectively actuating the motor 93. Furthermore, neither the motor 93 nor the stop brackets 97 and 98 generate any audible noise which could apprise the test subject that a stimulus point is being illuminated.

As shown in FIG. 3, the viewing screen 17 is provided with a screen light source 106. The light source 106 is driven by a variable voltage power source which is controlled by a knob on the control panel. Thus the test operator may select the screen illumination; in this manner, the contrast between the screen illumination, that is, the background illumination, and the stimulus intensity may be controlled.

The light source 106 is disposed at the upper edge of the screen 17. Directly adjacent to the light source 106 is a photoelectric cell 107, which is directed downwardly at the hemispheric screen 17. It may be appreciated that the light source 106, being adjacent to the photoelectric cell 107, cannot illuminate the photoelectric cell directly. Rather, the photoelectric cell receives light from the source 106 only after it has been reflected from the screen 17. The photoelectric cell 107 thus measures the background illumination of the screen 17. The output of the photoelectric cell 107 is amplified and displayed by the same digital meter on the control panel which displays the stimulus intensity. A switch on the control panel is provided so that the test operator may select the background intensity or the stimulus intensity as the display of the meter.

The visual field mapping device of the present invention also includes an eye attention module 110, which is disposed in the topographic center of the hemispheric screen 17. With reference to FIGS. 3, 9, and 10, the eye attention module includes a cylindrical tube 113 which extends through the screen 17 from the back side thereof. A collar 112 is secured about the tube 113, abutting the concave surface of the screen 17. Extending outwardly from the collar 112 is a hood 111, which is provided with an obliquely downwardly slanting end to shield the interior of the eye attention module from the light emanating from the screen light source 106.

The cylindrical member 113 houses a telescope which is directed toward the eye of the test subject. The telescope has a short focal length, and the image of the pupil of the eye is focussed on a four quadrant photocell detector. The signals from the four quandrant photocell detector are processed by the electronic circuitry to determine whenever the fixation of the eye of the test subject wanders from the center of the viewing screen, and also to determine whenever the eyelids close. In either event, the automatic testing sequence is interrupted, so that erroneous visual field data is avoided, in the former case, and so that the test subject may rest the eye being tested, in the latter case.

As shown in FIG. 9, a plano-convex objective lense 114 is disposed within the cylindrical member 113, comprising the objective lens of the telescope. Joined to the planar surface of the lens 114 is a tubular member 116, which is disposed concentrically about the optical axis of the telescope. The member 116 supports an objective lens 117, adjacent to an aperture 121 in the distal end of the member. Joined to the convex surface of the lens 114 is a cylindrical block 118 which supports one end of a light conducting fiber 119. The light conducting fiber 119 is aligned with the optical axis of the telescope and with the tubular member 116. The block 118 is transparent, and also supports a target transparency 122 which is illuminated by the light conducting fiber 119. The transparency 122 may be provided with a color unique to the testing scheme, such as red or blue, and may also be provided with a target image such as a cross-hair or the like.

The other end of the light conducting fiber 119 is connected to the screen light source, not shown in the figure. The target image may be interrupted periodically or aperiodically to renew stimulation of the eye of the test subject, and maintain eye fixation on the center of the viewing screen 17. It may be appreciated that the lenses 114 and 117 project the image of the target transparency 122 to the eye of the test subject, as shown in FIG. 9.

As shown in FIG. 11, the control portion of the present invention includes a control logic 125 which is provided with a built-in algorithm to operate the automatic testing sequence of the invention. Both the attention monitor 110 and the subject response pushbutton 20 are connected to the control logic 125. The control logic is also connected to the shutter motor 93, the selector motor 41, and through the contact pads 54 and 56 to the marking resistors of the mapping device 16.

The control system includes an address counter 126 which stores the address of the currently-actuated stimulus point, and which may be incremented upwardly by connection with the contacts 58 and 59, as explained in the foregoing. The address counter may also be reset to zero through connection to contact 61, also as explained in the foregoing. The address counter is connected to a current address display 127, which comprises a digital meter on the control panel. A pair of binary coded decimal address select switches 128 are also disposed on the control panel, to provide for manual selection of stimulus points to be tested. The switches 128 are connected to an address comparator 129, which is also connected to the address counter 126. The output of the address comparator 129, which represents a match between the counter contents and the selector switch settings, is connected to the control logic. It may be understood that in the manual selection mode, the switches 128 may be set for any stimulus point number, and the control logic will actuate the selector motor to rotate the arm 46 until it arrives at the selected address.

FIG. 12 depicts a flow chart of the algorithm embodied in the control logic 125, which operates the automatic test sequence of the present invention. To start the algorithm, the arm 46 is rotated to the zero address, as indicated by the contact 61. The subject response push button 20 is then enabled. Following this event, the shutter mechanism is opened and the duration delay which maintains opening of the shutter is actuated.

Next, a response from the test subject is awaited. If there is a response while the shutter is open, the map marking resistor corresponding to the stimulus point being illuminated is actuated. At the same time, the control logic awaits the end of the duration time delay. While the duration time delay is in effect, the information from the eye attention module is processed to determine eye fixation. If there is lack of eye fixation, the shutter is closed, the stimulus duration is suspended, and an audible alarm sounds. This condition is maintained as long as there is lack of eye fixation. When eye fixation is restored, the shutter is opened once more, the duration time delay is continued, and the audible alarm is disabled.

When the duration time delay is ended, or the map marking procedure is ended, the shutter is closed by the motor 93, a random time delay is initiated, and the subject response push button 20 is disabled. When the random time delay has ended, and the map marking procedure is completely finished, the motor 41 is actuated to rotate the arm 46 to the next stimulus point address. When the address in the address counter 126 equals N plus 1, that is, the previous address plus 1, the motor 41 is stopped and the contents of the address counter 126 is checked. If the address counter contents equals ninety-nine, indicating that all the stimulus points have been tested, the automatic testing sequence is finished and an audible alarm sounds. If the address counter contents does not equal ninety-nine, the algorithm goes through a loop and returns to point A on the flow chart shown in FIG. 12. The loop then iterates once more and as many times as necessary until all of the stimulus test points have been illuminated.

It may be appreciated that lack of subject response to illumination of a stimulus test point may be the result of inattention or fatigue and not necessarily indicative of any physiological problem. Thus a retest of the stimulus points missed by the subject is useful in eliminating spurious data and providing a more accurate map of the visual field.

The program of the present invention easily lends itself to this task. A register may be provided to store the address of the current stimulus, and lack of response of the subject, indicated by completion of the duration delay, triggers the register to store that address. At the end of the test procedure, when N = 99 and before the test done alarm is actuated, the algorithm may be looped back to point A using the address or addresses stored in the register. Since the respective map marking register is uniquely associated with the retested stimulus point by the contacts on the distribution panel, a positive response will cause the proper mark to be made on the visual field map.

To emphasize the most significant aspects of the present invention, it should be noted that this visual field mapping device provides continuous monitoring of the luminance of the background lighting on the viewing screen, as well as the luminance of the visual stimulus points. Furthermore, the contrast lever between these two luminance levels may be adjusted by the operator to any desired contrast. This precise control of luminance levels provides for highly accurate replication of visual field mapping tests, so that variations in test results may be interpreted with a much greater degree of certainty. Furthermore, variations in the projection light source due to age or external factors may be easily corrected.

Also, the present invention provides a unique address for each stimulus test point, sot that each test point may be easily actuated in the manual mode. In the automatic test sequence, the unique address feature of the present invention determines that only the one correct stimulus test point may be illuminated at one time.

Further, it should be noted that the mechanism of the present invention is virtually noiseless, providing no audible cues to the test subject which might affect the outcome of the testing procedure. In this regard, the random time delay which is provided between illumination of stimulus test points disrupts any test rhythm which might be sensed by the test subject.

I claim:

1. A device for mapping the visual field of a test subject, comprising viewing screen means having a plurality of stimulus test points thereon; a plurality of light conducting fibers each joined at one end to one of said stimulus tests points; light module means for generating a light beam of selected luminance and color; light distribution means coupled to said light module means and the other ends of said light conducting fibers for selectively and individually illuminating the latter; address means associated with said light distribution means for electronically identifying each of said other ends of said light conducting fibers; and address counter means for storing the identity of said light conducting fiber being illuminated at any time; said light distribution means including a light distribution board, with said other ends of said light conducting fibers disposed in a circular array on said board, a scanning arm pivotally disposed at the center of said circular array, said scanning arm including a light conducting pipe for selectively registering with and illuminating each of said light conducting fibers individually; and wherein said address means includes circuit means disposed concentrically about said circular array, and contact means on said scanning arm for contacting said circuit means.

2. The device of claim 1 wherein said circuit means includes map marking circuit means, having marking points corresponding to said stimulus test points, including a plurality of contact pads each associated with one of said light conducting fibers in said circular array, and one of said map marking points.

3. The device of claim 1 wherein said contact means on said scanning arm includes at least one brush for completing a circuit through one of said contact pads to one of said map marking points.

4. The device of claim 1, wherein said circuit means includes a plurality of address contacts disposed adjacent to said circular array, and said scanning arm includes at least one brush for contacting said address contacts.

5. The device of claim 4, wherein said at least one brush is connected to said address counter means to increment said address counter means.

6. The device of claim 1, wherein said address counter means includes an address comparator coupled thereto, and at least one binary coded decimal manual input switch coupled to said address comparator, and motor means in said light distribution means for scanning said address means until the setting of said manual input switch equals the contents of said address counter means.

7. A device for mapping the visual field of a test subject, comprising viewing screen means having a plurality of stimulus test points thereon; a plurality of light conducting fibers each joined at one end to one of said stimulus test points; light module means for generating a light beam of selected luminance and color; light distribution means coupled to said light module means and the other ends of said light conducting fibers for selectively and individually illuminating the latter; address means associated with said light distribution means for electronically identifying each of said other ends of said light conducting fibers; address counter means for storing the identity of said light conducting fiber being illuminated at any time, first photoelectric means associated with said light module means for determining the luminance of said light beam emanating from said light module means, screen lighting means for illuminating said viewing screen means with a selectively variable background luminance, and second photoelectric means for determining the luminance of said background illumination of said viewing screen means.

8. The device of claim 7, further including shutter means associated with said lighting module for selectively blocking said light beam from impinging on said light distribution means.

9. The device of claim 7, further including continuously variable neutral density filter means associated with said light module means for interfering with said light beam and selectively varying the luminance thereof.

10. The device of claim 7, further including color filter means associated with said light module means for altering the color of said light beam emanating therefrom.

11. The device of claim 7, further including eye attention monitor means for determining that the eye of the test subject is fixated on a central spot on said viewing screen means.

12. The device of claim 11, further including a target image associated with said eye attention monitor means for fixating the eye of said subject.

13. The device of claim 11, wherein said eye attention monitor means includes a telescope trained on the eye of the test subject, and third photoelectric means disposed at the image plane of said telescope.

14. The device of claim 13, wherein said target image is disposed in the center of the objective lens of said telescope.

15. The device of claim 7, further including visual field map fabricating means for making a graphical representation of said visual stimulus test points observed by the test subject, and subject response means for actuating said visual field map fabricating means.

16. The device of claim 15, wherein said visual field map fabricating means includes a plurality of marking points, each corresponding to one of said visual stimulus test points, and a web form for being imprinted by said test points.

* * * * *